(12) United States Patent
Kroll et al.

(10) Patent No.: US 7,123,961 B1
(45) Date of Patent: Oct. 17, 2006

(54) STIMULATION OF AUTONOMIC NERVES

(75) Inventors: Mark W. Kroll, Simi Valley, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 207 days.

(21) Appl. No.: 10/841,094

(22) Filed: May 7, 2004

Related U.S. Application Data

(63) Continuation of application No. 10/172,824, filed on Jun. 13, 2002, now abandoned.

(51) Int. Cl.
*A61N 1/362* (2006.01)

(52) U.S. Cl. .................... 607/9; 607/50; 607/2

(58) Field of Classification Search ............ 607/2, 607/9, 11, 17, 25, 28, 118
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 5,203,326 A * | 4/1993 | Collins | 607/4 |
| 5,334,221 A | 8/1994 | Bardy | |
| 5,356,425 A | 10/1994 | Bardy et al. | |
| 5,411,531 A | 5/1995 | Hill et al. | |
| 5,466,254 A | 11/1995 | Helland | 607/123 |
| 5,476,483 A | 12/1995 | Bornzin et al. | 607/17 |
| 5,507,784 A | 4/1996 | Hill et al. | |
| 5,700,282 A | 12/1997 | Zabara | |
| 6,027,456 A | 2/2000 | Feler et al. | |
| 6,073,048 A * | 6/2000 | Kieval et al. | 607/17 |
| 6,314,323 B1 | 11/2001 | Ekwall | 607/23 |
| 6,341,236 B1 * | 1/2002 | Osorio et al. | 607/45 |
| 2003/0078623 A1 * | 4/2003 | Weinberg et al. | 607/9 |

FOREIGN PATENT DOCUMENTS

| | | |
|---|---|---|
| EP | 0 547 734 A2 * | 7/1992 |
| WO | WO 94/00192 | 1/1994 |
| WO | WO 00/02623 | 1/2000 |
| WO | WO 01/00273 | 1/2001 |

OTHER PUBLICATIONS

Robert P. Frantz MD, "Beta Blockade in Patients with Congestive Heart Failure," Postgrad. Med. 2000; 108(3):103-118.
Dainius H. Pauza et al., "Morphology, Distribution, and Variability of the Epicardiac Neural Ganglionated Subplexuses in the Human Heartr" *The Anatomical Record*, 2000; vol. 259(4), pp. 353-382.
Nicholas James Mizeres, "The Cardiac Plexus in Man," Amer. J. of Anatomy, 1963; 112:141-151.
Masahiko Murakami MD, et al., "Effects of Cardiac Sympathetic Nerve Stimulation on the Left Ventricular End-Systolic Pressure-Volume Relationship and Plasma Norepinephrine Dynamics in Dogs," *Jpn Circ J*, 1997; vol. 61(10), pp. 864-871.

(Continued)

*Primary Examiner*—Carl H. Layno

(57) ABSTRACT

An exemplary method for stimulating an autonomic nerve that includes delivering power to, for example, an electrode at a set power level, determining whether the delivering achieved an autonomic response that affected cardiac function, and delivering power to the electrode at a reduced power level if the delivering affected the cardiac function. An exemplary device for performing such an exemplary method. Other exemplary methods and exemplary devices are also disclosed.

36 Claims, 9 Drawing Sheets

OTHER PUBLICATIONS

Xiao-Jun Du et al., "Response to Cardiac Sympathetic Activation in Transgenic Mice Overexpressing β2-Adrenergic Receptor", *Am J Physiol*, 1996; vol. 271(8), No. 2, Part 2, pp. H630-H636.

Hiroshi Miyano et al., *"Dynamic sympathethic Regulation of Left Ventricular Contractility Studied in the Isolated Canine Heart,"* Am. J. Physiol., 1998; 275: H400-H408.

Fany A. Kralios, et al., "Local Ventricular Repolarization Changes Due to Sympathetic Nerve-Branch Stimulation," *American Journal of Physiology*, May 1975; vol. 228, No. 5, pp. 1621-1626.

J. Andrew Armour, "Myocardial Ischaemia and the Cardiac Nervous System," *Cardiovascular Research*, 1999; vol. 41, pp. 41-54.

\* cited by examiner

EXEMPLARY STIMULATION PULSES

STIMULATION OF AUTONOMIC NERVES

CROSS-REFERENCE TO RELATED APPLICATIONS

This application is a continuation of copending U.S. patent application Ser. No. 10/172,824, filed Jun. 13, 2002 now abandoned.

TECHNICAL FIELD

The various methods and/or devices described herein generally relate to cardiac pacing and/or stimulation therapy. More particularly, such methods and/or devices related to methods and/or implantable stimulation devices for stimulating autonomic nerves.

BACKGROUND

The autonomic nervous system includes sympathetic and parasympathetic pathways. Stimulation of nerves in these pathways can affect cardiac operation or function. In general, sympathetic activation causes an increase in heart rate and inotropy (contractility) and hence cardiac output. Frantz, "Beta blockade in patients with congestive heart failure," Postgraduate Medicine, 108(3), 103–118 (2000), explains that "[i]n a teleological sense, an acute increase in sympathetic drive was advantageous for our ancestors. When they were being pursued by a tiger or bleeding from a wound, increasing heart rate, peripheral tone, and myocardial contractility allowed them to reach safety or maintain central perfusion." In contrast, parasympathetic activation generally causes a decrease in atrial rate and contractile force, atrio-ventricular nodal conduction, and ventricular contractile force. Hence, selective activation or stimulation of the autonomic nerves can provide a means for cardiac control. While reports of autonomic nerve stimulation are known, a need exists for setting stimulation parameters (e.g., power level, thresholds, etc.), especially when stimulation occurs via an implantable device with a limited power supply.

SUMMARY

An exemplary method for delivering power to an electrode for stimulating an autonomic nerve to affect cardiac function that includes delivering power to the electrode at a set power level, determining whether the delivering achieved an autonomic response that affected cardiac function, and delivering power to the electrode at a reduced power level if the delivering affected the cardiac function. An exemplary device for performing such an exemplary method is also described herein. Other exemplary methods and exemplary devices are also disclosed.

The various exemplary devices and exemplary methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate or shock a patient's heart.

Figure 1:
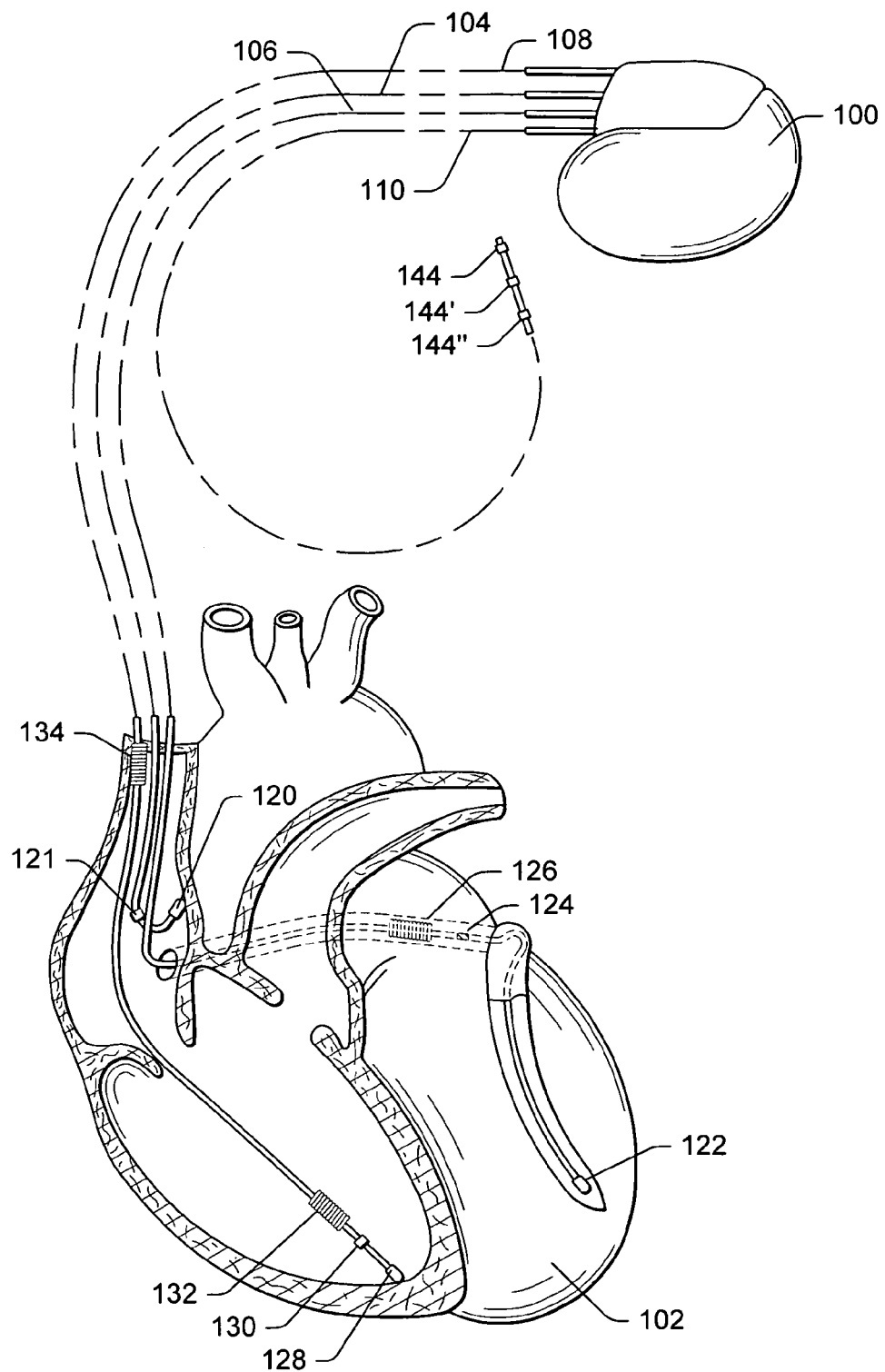
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of sympathetic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
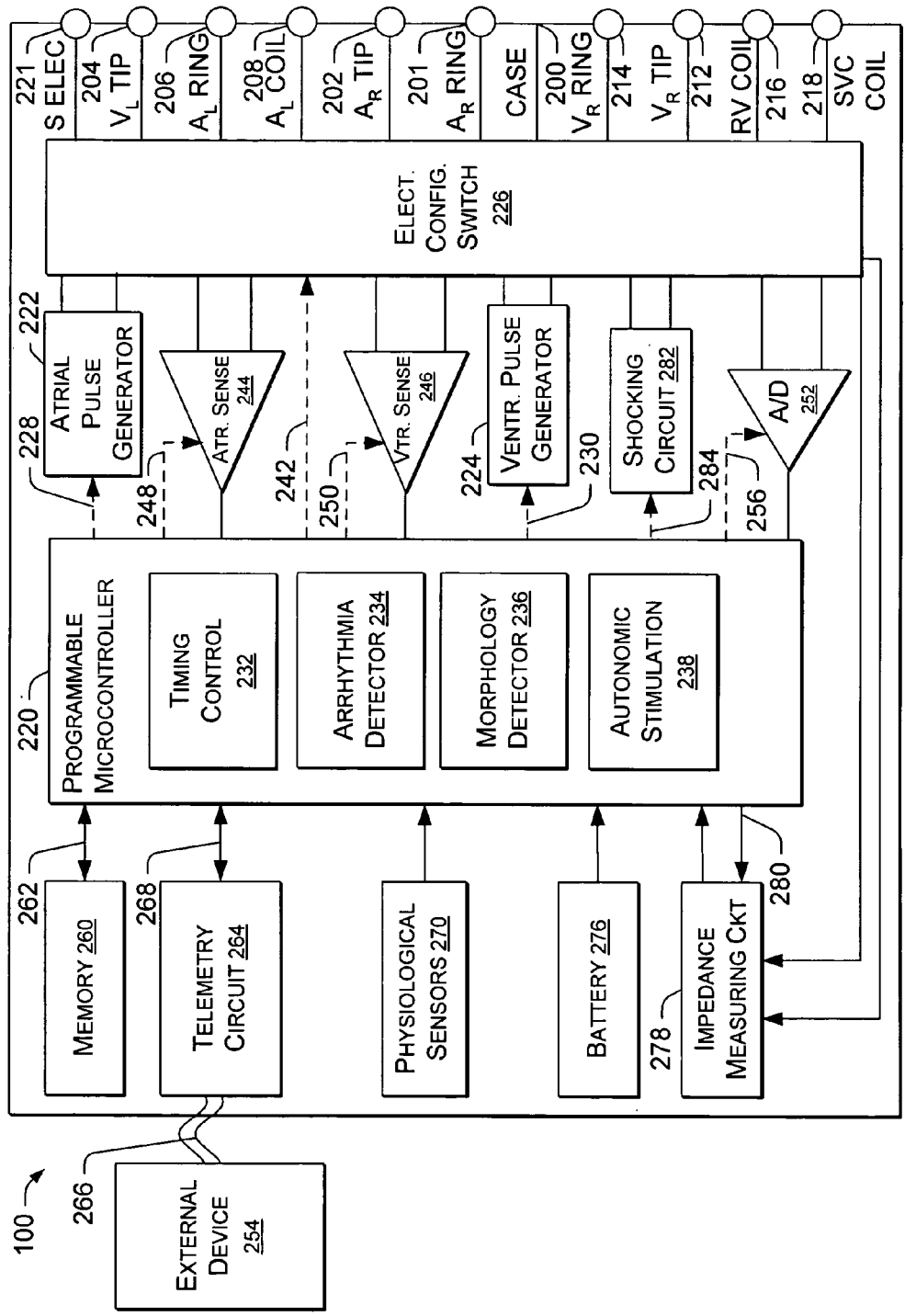
FIG. 2 is a functional block diagram of an exemplary implantable stimulation device illustrating basic elements that are configured to provide cardioversion, defibrillation, pacing stimulation and/or autonomic nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. In such instance, delivery of a stimulus to an autonomic nerve may achieve an autonomic response. In addition, such an autonomic response may affect cardiac function. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or sympathetic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or sympathetic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, sympathetic stimulation to, for example, increase contractility or rate of a patient's heart and/or parasympathetic stimulation to, for example, decrease rate of a patient's heart. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, generally suppress atrial rate and contractile force, atrio-ventricular nodal conduction, and ventricular contractile force, also known as contractility or inotropy. Sympathetic efferent postganglionic neurons, when stimulated, generally increase heart rate and increase contractility. Note that contractility is associated with the term "inotropy", heart rate is associated with the term "chronotropy" and conduction velocity is associated with the term "dromotropy."

As already mentioned, stimulation of parasympathetic nerves acts to decrease heart rate while stimulation of sympathetic nerves acts to increase heart rate. Regarding sympathetic stimulation, action occurs primarily through release of norepinephrine, which acts on the sinoatrial node (SA node) to increase the rate of diastolic depolarization, and thereby increase heart rate, and acts on the atrioventricular node (AV node) to increase the velocity of conduction and diminish the refractory period during which the AV node is typically unresponsive to stimuli coming from the atrium.

Contractility (or inotropy) refers to the force or strength of cardiac muscle contractions. Stimulation of sympathetic nerves causes active contractility whereas Frank-Starling mechanism causes passive contractility. Active contractility involves norepinephrine, which increases myocardial calcium permeability (or conductance) and hence actin/myosin crossbridge interactions. Other mechanisms may also accompany the increase in calcium permeability.

In general, an increase in ventricular contractility causes an increase stroke volume, which, in turn, can increase cardiac output. Cardiac output (CO) depends on heart rate (HR) and stroke volume (SV) (e.g., CO equals HR times SV). Changes in ventricular contractility alter the rate of force and pressure development by the ventricle and therefore change the rate of ejection (i.e., ejection velocity). For example, an increase in contractility shifts the Frank-Starling curve, which causes a reduction in end-systolic volume and an increase in stroke volume. The increased stroke volume also causes a reduction in ventricular end-diastolic volume (i.e., preload). The end-systolic pressure-volume relationship (ESPVR) may define an inotropic state of the ventricle.

Changes in contractility also produce significant changes in ejection fraction (EF). Increasing contractility leads to an increase in EF, while decreasing contractility decreases EF. Therefore, EF is often used as a clinical index for evaluating the inotropic state of the heart. In heart failure, for example, an associated decrease in contractility leads to a fall in stroke volume as well as an increase in preload, thereby decreasing EF. The increased preload, if it results in a left ventricular end-diastolic pressure greater than approximately 20 mmHg, can lead to pulmonary congestion and edema. Treatment of a patient in heart failure with an inotropic drug (e.g., beta-adrenoceptor agonist or digoxin) shifts the depressed Frank-Starling curve up and to the left, thereby increasing stroke volume, decreasing preload, and increasing EF.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Figure 3:
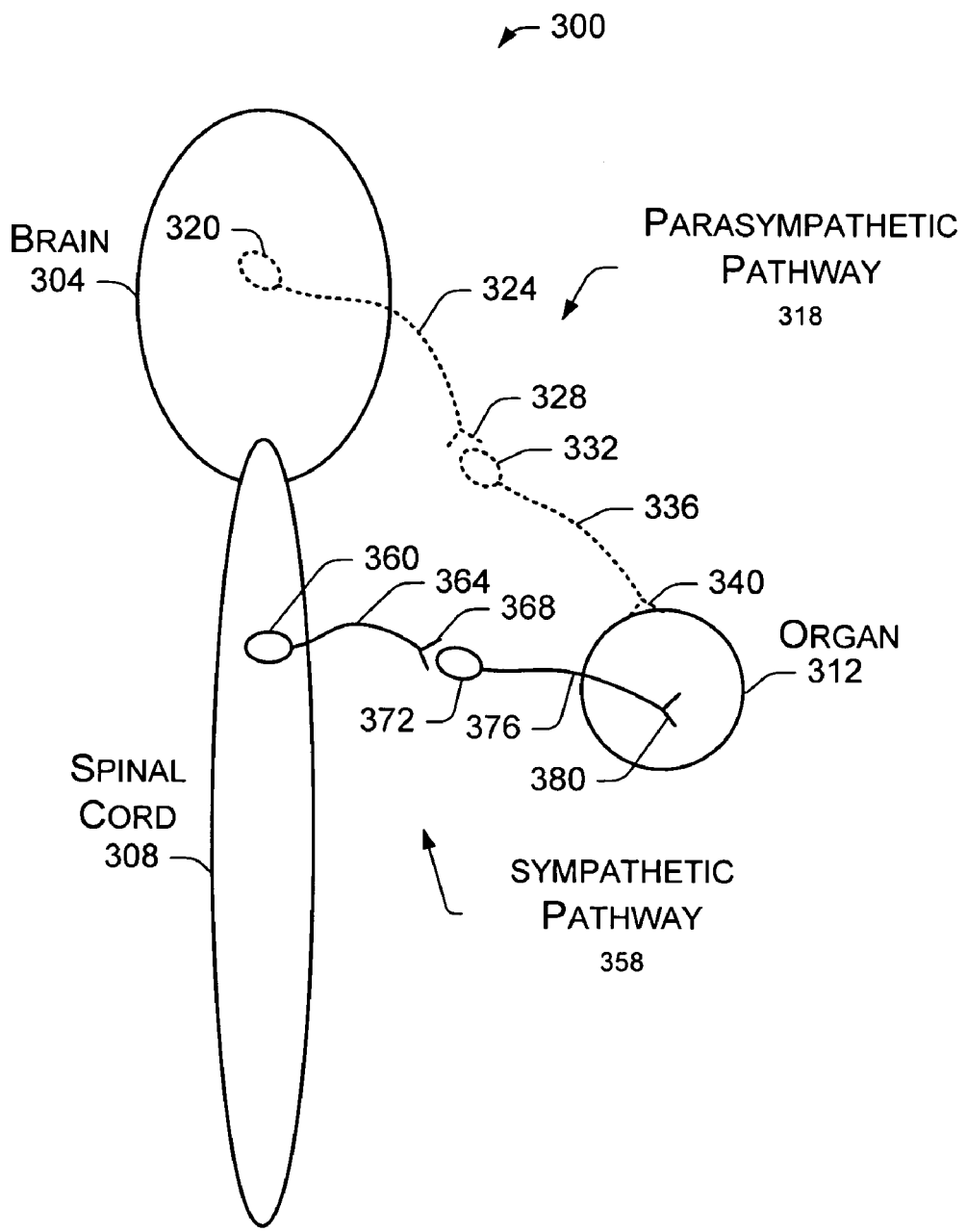
FIG. 3 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 3, a simplified diagram of the autonomic nervous system 300 is shown. The system 300 illustrated includes a brain 304, a spinal cord 308, an organ 312, a parasympathetic efferent pathway 318 and a sympathetic efferent pathway 358. The parasympathetic efferent pathway 318 includes a preganglionic cell body 320 located in the brain 304, a preganglionic axon 324, a synaptic cleft 328, a postganglionic cell body 332, a postganglionic axon 336, and a postganglionic synaptic cleft 340 proximate to the organ 312. An exemplary parasympathetic stimulus originates at the brain 304 and ends at the postganglionic synaptic cleft 340 wherein a chemical is emitted to effect cells of the organ 312. A synaptic cleft may also be referred to as a neuroeffector junction. The sympathetic efferent pathway 358 includes a preganglionic cell body 360 located in the spinal cord 308, a preganglionic axon 364, a synaptic cleft 368, a postganglionic cell body 372, a postganglionic axon 376, and a postganglionic synaptic cleft 380 proximate to the organ 312. An exemplary sympathetic stimulus originates at the spinal cord 308 and ends at the postganglionic synaptic cleft 380 wherein a chemical is emitted to effect cell of the organ 312. In both pathways 318, 358, acetylcholine operates as a neurotransmitter to activate postganglionic neurons, i.e., preganglionic neurons are cholinergic. In parasympathetic pathways (e.g., the parasympathetic pathway 318), postganglionic neurons emit acetylcholine and are therefore cholinergic. However, in many sympathetic pathways (e.g., the sympathetic pathway 358), postganglionic neurons emit norepinephrine and are therefore adrenergic. While FIG. 3 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32. Parasympathetic and sympathetic pathways having cardiac effect are described in more detail below.

Parasympathetic Pathways

In physiological terms, the parasympathetic system is concerned with conservation and restoration of energy, as it causes a reduction in heart rate and blood pressure, and facilitates digestion and absorption of nutrients, and consequently the excretion of waste products. The preganglionic outflow of the parasympathetic nervous system arises from the cell bodies of the motor nuclei of the cranial nerves III, VII, IX and X in the brain stem and from the second, third and fourth sacral segments of the spinal cord. It is therefore also known as the cranio-sacral outflow.

The cranial nerve X, known as the vagus nerve, carries fibres to the heart, lungs, stomach, upper intestine and ureter. The vagus nerve has two branches (right vagus nerve and left vagus nerve) which make up 75% of all parasympathetic fibers passing to the thoracic and abdominal regions of the body. The right and left vagus nerves may be distributed differently according to the embryological origin of the SA and AV nodes. Each vagus nerve contains both somatic and autonomic branches, however within the body the autonomic function predominates. As is the case with most nerves, vagi nerves contain both efferent fibers, carrying impulses from its origin in the medulla obligata of the brain to a tissue or visceral organ, as well as afferent fibers, which carry the impulse from the organ back to the brain itself. With vagus nerves, 80% of the fibers are afferent as opposed to efferent. This aids in their active response to the many reflex actions in the body during parasympathetic control.

In the adult the right vagus nerve innervates mainly the SA node and the left vagus innervates the AV node. More specifically, the right vagus nerve innervates the SA node, the atrial muscle and, to a much lesser degree, the AV node while the left vagus nerve innervates the SA node and atrial muscle to a lesser degree than it innervates the AV node. In general, stimulation of the right vagus nerve predominately slows the SA node rate and thereby reduces heart rate. Stimulation of the left vagus nerve produces some slowing of the SA node, prolongation of AV conduction and partial or total AV block. The resting heart is normally under the influence of some parasympathetic stimulation. With normal vagal tone, the resting heart rate is about 70 beats per minute (bpm). If vagal influences are blocked, the heart rate increases to approximately 150 bpm to approximately 180 bpm due to sympathetic tone.

The chemical transmitter at both pre- and postganglionic synapses in the parasympathetic system is acetylcholine; thus, the receptors are cholinergic. The specific acetylcholine receptors have been subdivided pharmacologically by the actions of the alkaloids muscarine and nicotine. Parasympathetic cholinergic muscarinic receptors act on the SA node, primarily via the right vagus nerve, to decrease heart rate and act on the AV node, primarily via the left vagus nerve, to decrease conduction velocity. Decreased conduction velocity in the AV node slows transmission of nerve impulses to the ventricles. Very strong stimulation of the vagus nerves can cause a complete stop of cardiac rhythm; however, in such instances, ventricular escape usually occurs within approximately 10 seconds. In addition, the SA and AV nodes are generally rich in cholinesterase, hence, the effects of released acetylcholine are usually ephemeral due to rapid hydrolysis.

Sympathetic Pathways

Figure 4:
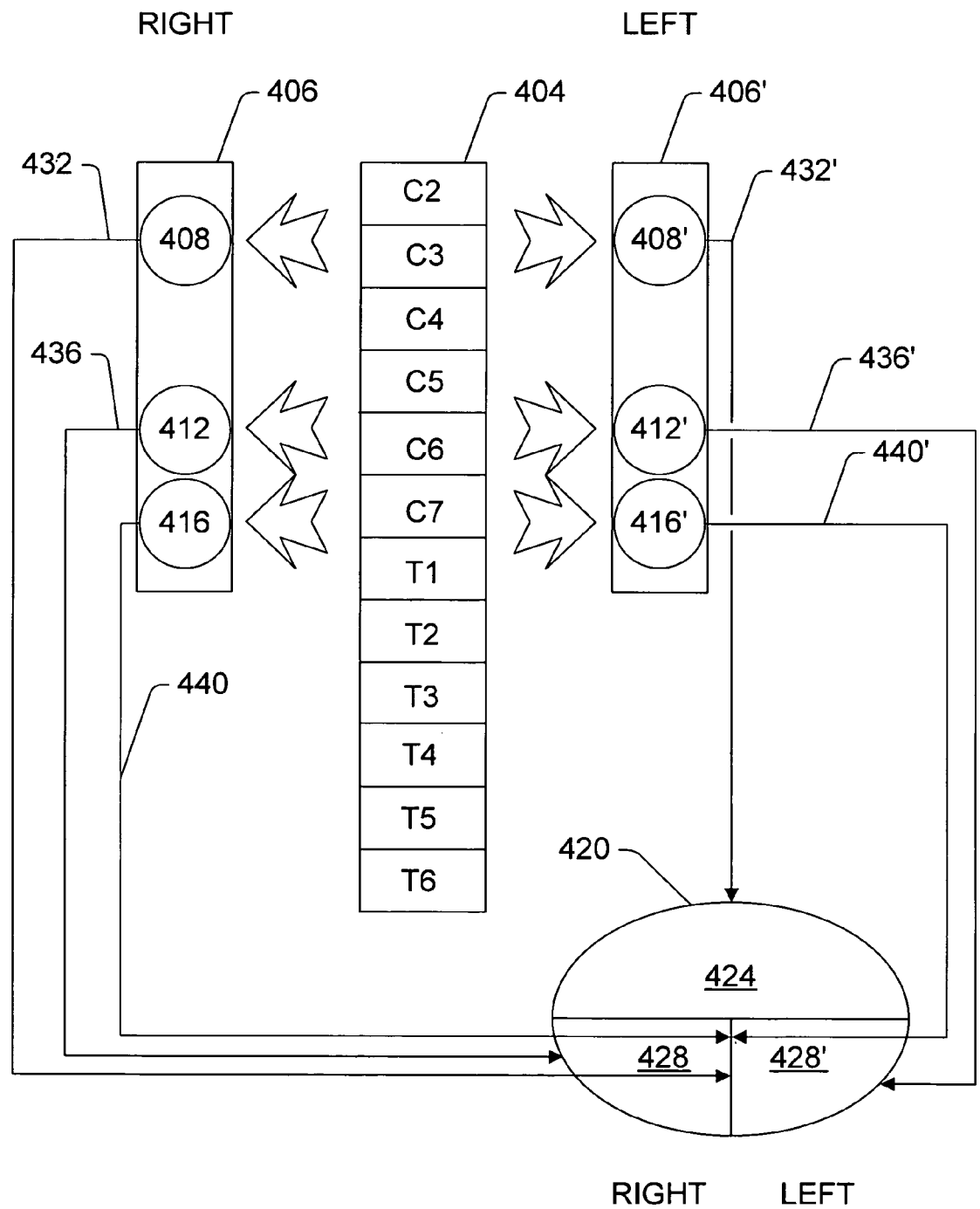
FIG. 4 is a simplified approximate anatomical diagram of sympathetic pathways to the heart.

Referring to FIG. 4, a block diagram of components of the sympathetic nervous system is shown. The sympathetic nervous system, which is not part of the central nervous system, includes two parallel chains or trunks, a right trunk 406 and a left trunk 406'. Each trunk includes a series of ganglia which lie just lateral to the spinal cord 404 on each side (left and right). In general, the uppermost region of each trunk (406, 406') has three cervical ganglia, which are continuous with the thoracic trunk. The cervical ganglia are known as the right and left superior cervical ganglia (408, 408'), the right and left middle cervical ganglia (412, 412') and the right and left inferior cervical ganglia (416, 416'), the latter of which are known as a stellate ganglion if they combine with a respective first thoracic ganglion. Stellate ganglia exist in approximately 70% to approximately 80% of the population.

Cardiac sympathetic fibers originate in intermediolateral columns of the upper five or six thoracic segments (see T1–T6 in FIG. 4) and lower one or two cervical segments (see C5 and C6 in FIG. 4) of the spinal cord 404. Sympathetic fibers enter the paravertebral chain and typically synapse in the cervical ganglia. Cardiac sympathetic ganglia are generally found close to the spinal column (paravertebral ganglia) and may stem from both thoracic and cervical preganglionic fibers. Postganglionic cardiac sympathetic nerves originate from the left and right ganglia and usually approach the base of the heart (e.g., as superior, middle, and inferior cardiac nerves) along the adventitial surface of the great vessels.

Each of the superior cardiac nerves 432, 432' arises by two or more branches from a respective superior cervical ganglion 408, 408', and occasionally receives a filament from the trunk between a first and/or a second cervical ganglia. The right superior cardiac nerve 432, at the root of the neck, passes either in front of or behind the subclavian artery, and along the innominate artery to the back of the arch of the aorta, where it joins the deep part 428, 428' of the epicardial plexus 420. The right superior cardiac nerve 432 connects with other sympathetic branches. About the middle of the neck the right superior cardiac nerve 432 receives filaments from the external laryngeal nerve; lower down, one or two twigs from the vagus; and as it enters the thorax it is joined by a filament from the recurrent nerve. In addition, filaments from the nerve communicate with the thyroid branches from the right middle cervical ganglion 412. The left superior cardiac nerve 408', in the thorax, runs in front of the left common carotid artery and across the left side of the arch of the aorta, to the superficial part 424 of the epicardial plexus 420.

Each of the middle cardiac nerves 436, 436' (or great cardiac nerves), the largest of the three cardiac nerves, arises from a respective middle cervical ganglion 412, 412', or from a respective trunk 406, 406' between the middle ganglion 412, 412' and the inferior ganglion 416, 416'. On the right side, the right middle cardiac nerve 436 descends behind the common carotid artery, and at the root of the neck runs either in front of or behind the subclavian artery; it then descends on the trachea, receives a few filaments from the recurrent nerve, and joins the right half of the deep part 428 of the epicardial plexus 420. In the neck, it communicates with the right superior cardiac nerve 432 and recurrent nerve. On the left side, the left middle cardiac nerve 436' enters the chest between the left carotid and subclavian arteries, and joins the left half of the deep part 428' of the epicardial plexus 420.

Each inferior cardiac nerve 440, 440' arises from the respective inferior cervical ganglion 416, 416' or the first thoracic ganglion (or stellate ganglion, e.g., 416, 416'). Both right and left inferior cardiac nerves 440, 440' descend behind the subclavian artery and along the front of the trachea, to join the deep part 428, 428' of the epicardial plexus 420. Each of the inferior cardiac nerves 440, 440' communicates freely behind the subclavian artery with the recurrent nerve and the respective middle cardiac nerve 436, 436'.

As already mentioned with reference to FIG. 4, at the base of the heart, the sympathetic fibers form an epicardial plexus 420 that distributes the fibers to the various regions of the heart. The epicardial plexus 420 has a superficial part 424 and a deep part (shown as a right deep part 428 and a left deep part 428' in FIG. 4), see, e.g., Gray's anatomy: the anatomical basis of medicine and surgery, 38th ed. (1995). The deep part 428, 428' lies upon the tracheal bifurcation (at the back of the aorta and in front of the tracheal bifurcation) and consists of cardiac branches from all cervical sympathetic ganglia of both right and left sides except the superior left 408', together with superior and inferior cervical and thoracic cardiac branches of the right vagus nerve (parasympathetic) and superior cervical and thoracic branches of the left vagus nerve (parasympathetic).

Pauza et al., "Morphology, distribution, and variability of the epicardiac neural ganglionated subplexuses in the human heart," The Anatomical Record 259(4): 353–382 (2000), reported that the epicardial plexus forms seven subplexuses: (I) left coronary, (II) right coronary, (III) ventral right atrial, (IV) ventral left atrial, (V) left dorsal, (VI) middle dorsal, and (VII) dorsal right atrial. Pauza et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza et al., also note that diagrams from Mizeres, "The cardiac plexus in man," Am. J. Anat. 112:141–151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava." Further, Pauza et al., also state that the left coronary (I), right coronary (II), ventral left atrial (IV) and middle dorsal (VI) subplexuses "may be considered as being formed by the deep extrinsic plexus that receives equally from both vagi and sympathetic trunks." Note that in the Pauza et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3 and FIG. 4. Thus, the term "postganglionic neurons" includes epicardiac/epicardial preganglionic neurons as well as epicardiac/epicardial postganglionic neurons.

Upon stimulation, end terminals (or terminal knobs) of the postganglionic sympathetic nerves (e.g., epicardial postganglionic sympathetic nerves) release norepinephrine, which acts upon the myocardium. Following stimulation and release, norepinephrine remains active for several seconds; norepinephrine may then be reabsorbed by the terminal, diffuse out of the area, or be inactivated by enzymes. The adrenal medulla also secretes norepinephrine (e.g., 75 percent epinephrine and 25 percent norepinephrine) and produces a peripheral effect that typically lasts much longer than that produced by stimulation of the sympathetic postganglionic terminal knobs. While circulating norepinephrine can increase contractility, the effect on normally innervated hearts is relatively minor with respect to norepinephrine released by end terminals. Heart rate, although initially stimulated by norepinephrine, usually decreases over time due to activation of baroreceptors and vagal-mediated (parasympathetic) slowing of the heart rate.

Cardiac tissue membrane receptors, such as alpha receptors and beta receptors, receive chemicals emitted by postganglionic nerves. Alpha receptors are the most common type of sympathetic receptor and they respond strongly to norepinephrine and weakly to epinephrine. Beta receptors are also adrenergic and include beta-1, beta-2 and beta-3 receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. In contrast, parasympathetic cholinergic muscarinic receptors act on the sinoatrial (SA) node to decrease heart rate and act on the atrioventricular (AV) node to decrease conduction velocity. Adrenergic antagonists (indirect action) include beta-blockers such as proranolol and alpha-blockers such as phentolamine that inhibit receptors. Cholinergic antagonists (indirect action) include alpha-blockers such as atropine.

Stimulation of nerves and/or tissue may occur through electrical and/or magnetic stimulation. In general, a magnetic field may stimulate a nerve and/or tissue. In addition, an electromagnetic field may stimulate a nerve and/or tissue. Yet further, direct electrical stimulation may stimulate a nerve and/or tissue. According to various exemplary methods and/or devices described herein, and/or structural and/or functional equivalents thereof, use electrical and/or magnetic stimulation of a nerve, nerves and/or tissue. While various exemplary methods and/or exemplary devices disclosed herein refer to use of one or more electrodes, coils and/or other electronics are optionally used to produce electric and/or magnetic fields capable of stimulating nerves and/or other tissue.

Electrical stimulation of autonomic nerves has been reported in the literature, see, e.g., Murakami et al., "Effects of cardiac sympathetic nerve stimulation on the left ventricular end-systolic pressure-volume relationship and plasma norepinephrine dynamics in dogs," Jpn. Circ. J. 61(10): 864–71 (1997); and Du et al., "Response to cardiac sympathetic activation in transgenic mice overexpressing beta 2-adrenergic receptor." Am-J-Physiol. Aug; 271(2 Pt 2): H630–6 (1996).

According to various exemplary methods and/or devices described herein, a series of pulses, or a pulse train, is typically delivered by an implantable stimulation device to stimulate an autonomic nerve. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency include frequencies ranging from approximately 0.1 to approximately 100 Hz, and, in particular, frequencies ranging from approximately 0.2 Hz to approximately 20 Hz, and more particularly, frequencies ranging from approximately 1 Hz to approximately 4 Hz. Of course, higher frequencies higher than 100 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 1.6 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 4 V to approximately 15 V.

For pulses delivered by implantable stimulation devices having a fixed or otherwise limited power supply, i.e., a power supply having power limitations, average power of a pulse or a pulse train is usually limited acutely by the power capability of the power supply (e.g., battery, fuel cell, nuclear generator, etc.) and chronically by the capacity of the power supply and desired longevity of the device's usefulness. Average power of a pulse is generally given as peak power averaged over one cycle. For example, given a voltage of 10 V, a resistance of 1000 ohms, a pulse frequency of 20 Hz and a pulse width of 1 ms, the peak power is given as voltage squared divided by resistance, which is 0.1 W, and the average power is 20 Hz multiplied by 1 ms multiplied by 0.1 W, which is 0.002 W or 2 mW. The term "power", as used herein, includes, but is not limited to, peak power and average power; thus, various exemplary methods are optionally suitable for use in setting, adjusting and/or determining peak power and/or average power.

Current drain is another factor often considered when determining power limitations of a power supply. Current drain is generally defined as the average amount of current drawn from a power supply in an implantable pulse generator in one hour. Current drain depends on many factors, including how frequently the device delivers pulses and at what parameters, the circuitry and/or the type of stimulation lead. Current drain is commonly expressed in millionths of an ampere or microamperes. A power drain based on current drain may be determined by the product of current drain and voltage. Such a power is optionally useful in determining a maximum power level for an autonomic stimulation pulse or pulses.

In general, a maximum power level or maximum power demand for an implantable device may be determined, in part, by the product of the voltage times the current capability of the battery (or other power supply) less circuit inefficiencies. Of course, desired power supply life (e.g., battery life) and/or other factors may be considered. For example, some implantable stimulation devices have a continuous power drain for one function (e.g., to drive a microchip, microprocessor or timing circuitry) and an intermittent function (e.g., such as pacing, measuring, signaling, etc.) which has intermittent power utilization. Consideration of such factors may be necessary in determining a tolerable and/or maximum power level and, in particular, in determining pulse parameters for autonomic nerve stimulation.

Right Sympathetic Pathway Stimulation

Referring again to FIG. 4, right sympathetic pathways are shown. The right cervical ganglia include the right superior cervical ganglion 408, the right middle cervical ganglion 412 and the right inferior cervical ganglion 416, the latter of which is known as the right stellate ganglion if it combines with the right first thoracic ganglion. As described herein, the ganglion labeled 416 represents the right inferior cervical ganglion, the right stellate ganglion and/or the right first thoracic ganglion.

In general, stimulation of right sympathetic nerves causes a pronounced increase in heart rate and a lesser increase in inotropy whereas stimulation of left sympathetic nerves causes a lesser increase in heart rate and a pronounced increase in inotropy, see, e.g., Miyano et al., "Dynamic sympathetic regulation of left ventricular contractility studied in the isolated canine heart," Am. J. Physiol., 275: H400–H408 (1998); Armour, "Myocardial ischaemia and the cardiac nervous system," Cardiovascular Research, 41: 41–54 (1999); and Kralios et al., "Local ventricular repolarization changes due to sympathetic nerve-branch stimulation," American J. Physiology, 228(5):1621–1626 (1975). According to Armour, stimulation of right sympathetic nerves (e.g., stemming from the right sympathetic trunk 406) typically yields a pronounced effect on heart rate and according to Kralios et al., "right-stellate cardiac nerve stimulation always resulted in marked sinus tachycardia." Kralios et al., further reported that "sympathetic fibers on the right side which alter recovery properties of the ventricular myocardium are distributed mostly via the recurrent cardiac nerve."

Right Superior Cervical Ganglion and Right Superior Cardiac Nerve

As shown in FIG. 4, the right superior cardiac nerve 432 arises by two or more branches from the right superior cervical ganglion 408, and occasionally receives a filament from the right trunk 406 between a first and/or a second cervical ganglia. The right superior cardiac nerve 432, at the root of the neck, passes either in front of or behind the subclavian artery, and along the innominate artery to the back of the arch of the aorta, where it joins the deep part (e.g., 428 and/or 428') of the epicardial plexus 420.

Stimulation of the right superior cervical ganglion 408 and/or the right superior cardiac nerve 432 is highly likely to cause stimulation of additional sympathetic branches and/or parasympathetic branches. For example, about the middle of the neck the right superior cardiac nerve 432 receives filaments from the external laryngeal nerve; lower down, one or two twigs from the vagus; and as it enters the thorax it is joined by a filament from the recurrent nerve (which branches from the vagus and surrounds the arterial duct). In addition, filaments from the nerve communicate with the thyroid branches from the right middle cervical ganglion 412. Thus, stimulation of the right superior cervical ganglion 408 and/or the right superior cardiac nerve 432 may also cause stimulation of the right middle cardiac nerve 436 and/or parasympathetic nerves (e.g., vagus nerve, recurrent nerve). Ultimately, supra-threshold stimulation of the right superior cervical ganglion 408 and/or the right superior cardiac nerve 432 will cause activation of nerves in the deep part 428, 428' of the epicardial plexus 420. Of course, electrodes may be positioned to minimize and/or eliminate stimulation of certain nerves (e.g., parasympathetic, left sympathetic, etc.).

Right Middle Cervical Ganglion and Right Middle Cardiac Nerve

Figure 7:
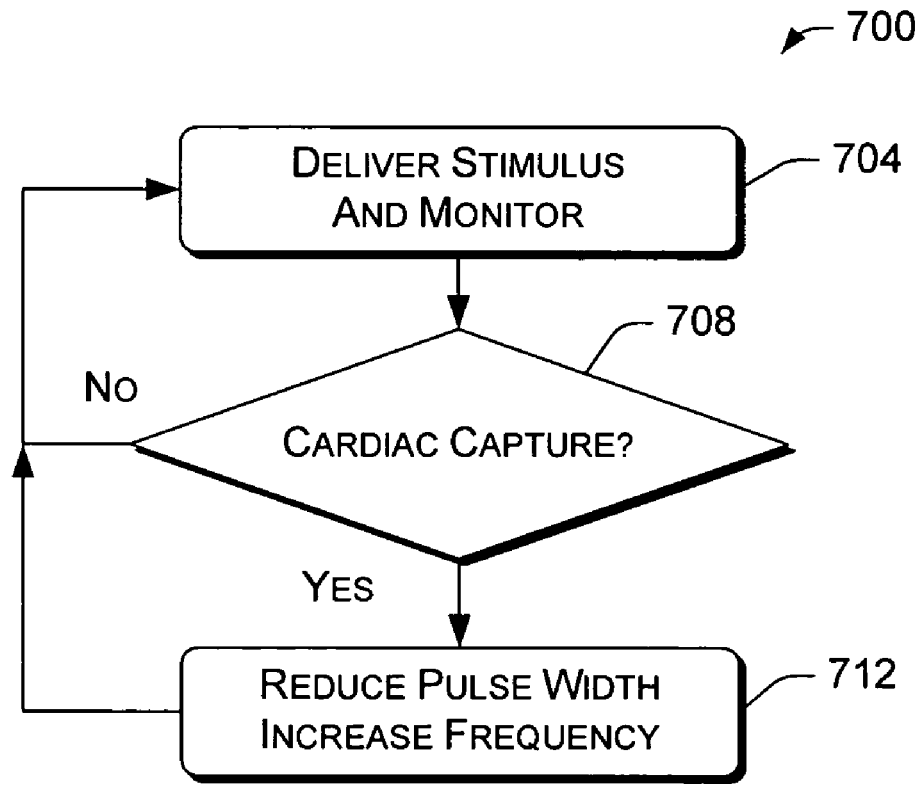
FIG. 7 is a block diagram of an exemplary method for avoiding cardiac capture due to autonomic nerve stimulation pulses.

The right middle cardiac nerve 436 (or right great cardiac nerve), arises from the right middle cervical ganglion 412, or from the right trunk 406 between the right middle ganglion 412 and the right inferior ganglion 416 (see, e.g., FIG. 7). The right middle cardiac nerve 436 descends behind the common carotid artery, and at the root of the neck runs either in front of or behind the subclavian artery; it then descends on the trachea, receives a few filaments from the recurrent nerve, and joins the right half of the deep part 428 of the epicardial plexus 420. In the neck, it communicates with the right superior cardiac nerve 432 and recurrent nerve. Thus, supra-threshold stimulation of the right middle cervical ganglion 412 and/or the middle cardiac nerve 436 may also cause stimulation of the right superior cardiac nerve 408 and/or the recurrent nerve. Ultimately, supra-threshold stimulation of the right middle cervical ganglion 412 and/or the right middle cardiac nerve 436 will cause activation of nerves in the right half of the deep part 428 of the epicardial plexus 420. Of course, electrodes may be positioned to minimize and/or eliminate stimulation of certain nerves (e.g., parasympathetic, left sympathetic, etc.).

Right Inferior Cervical Ganglion and Right Inferior Cardiac Nerve

The right inferior cardiac nerve 440 arises from the right inferior cervical ganglion 416 or the first thoracic ganglion (or the right stellate ganglion 416). The right inferior cardiac nerve 440 descends behind the subclavian artery and along the front of the trachea, to join the deep part 428, 428' of the epicardial plexus 420. The right inferior cardiac nerve 440 communicates freely behind the subclavian artery with the recurrent nerve and the right middle cardiac nerve 436. Thus, supra-threshold stimulation of the right inferior cervical ganglion 416 (or right stellate ganglion or right first thoracic ganglion) and/or the right inferior cardiac nerve 440 may also cause stimulation of the right middle cardiac nerve 412 and/or the recurrent nerve. Ultimately, supra-threshold stimulation of the right inferior cervical ganglion 416 (or right stellate ganglion or right first thoracic ganglion) and/or the right inferior cardiac nerve 440 will cause activation of nerves in the deep part 428, 428' of the epicardial plexus 420. Of course, electrodes may be positioned to minimize and/or eliminate stimulation of certain nerves (e.g., parasympathetic, left sympathetic, etc.).

Epicardial Right Sympathetic Pathways

As already mentioned, the ventral and dorsal right epicardial subplexuses (see, e.g., Pauza et al., supra) should be considered as being supplied by nerves of the right sympathetic pathways. Thus, according to various exemplary methods and/or devices described herein, direct stimulation of these epicardial subplexuses, and/or nerves extending from these subplexuses, will cause an increase in heart rate.

Left Sympathetic Pathway Stimulation

Referring again to FIG. 4, left sympathetic pathways are shown. The left cervical ganglia include the left superior cervical ganglion 408', the left middle cervical ganglion 412' and the left inferior cervical ganglion 416', the latter of which is known as the left stellate ganglion if it combines with the left first thoracic ganglion. As described herein, the ganglion labeled 416' represents the left inferior cervical ganglion, the left stellate ganglion and/or the left first thoracic ganglion.

In general, stimulation of right sympathetic nerves causes a pronounced increase in heart rate and a lesser increase in inotropy whereas stimulation of left sympathetic nerves causes a lesser increase in heart rate and a pronounced increase in inotropy, see, e.g., Miyano et al., "Dynamic sympathetic regulation of left ventricular contractility studied in the isolated canine heart," Am. J. Physiol., 275: H400–H408 (1998); Armour, "Myocardial ischaemia and the cardiac nervous system," Cardiovascular Research, 41: 41–54 (1999); and Kralios et al., "Local ventricular repolarization changes due to sympathetic nerve-branch stimulation," American J. Physiology, 228(5):1621–1626 (1975). According to Armour, stimulation of left sympathetic nerves (e.g., stemming from the left sympathetic trunk 406') typically yields a pronounced effect on contractility and according to Kralios et al., left-stellate cardiac nerve stimulation "caused atrioventricular junctional tachycardia, but no changes in electrocardiographic waveform." In addition, stimulation of the left ventrolateral nerve resulted in significant and more pronounced shortening of refractory periods than stimulation of stellate cardiac nerves. Kralios et al., further reported that "on the left side, sympathetic fibers that innervate the ventricular myocardium are distributed via the ventrolateral cardiac nerve and to a lesser extent via the ventromedial nerve" wherein little overlap exists between the recurrent cardiac ventrolateral nerves.

Left Superior Cervical Ganglion and Left Superior Cardiac Nerve

The left superior cardiac nerve 432' arises by two or more branches from the left superior cervical ganglion 408', and occasionally receives a filament from the trunk between a first and/or a second cervical ganglia. The left superior cardiac nerve 408', in the thorax, runs in front of the left common carotid artery and across the left side of the arch of the aorta, to the superficial part 424 of the epicardial plexus 420. Thus, supra-threshold stimulation of the left superior cervical ganglion 408' and/or the left superior cardiac nerve 432' will cause activation of nerves in the superficial part 424 of the epicardial plexus 420. Of course, electrodes may be positioned to minimize and/or eliminate stimulation of certain nerves (e.g., parasympathetic, right sympathetic, etc.).

Left Middle Cervical Ganglion and Left Middle Cardiac Nerve

The left middle cardiac nerve 436' (or left great cardiac nerve), the largest of the three cardiac nerves, arises from the left middle cervical ganglion 412', or from the left trunk 406' between the left middle ganglion 412' and the left inferior ganglion 416'. On the left side, the left middle cardiac nerve 436' enters the chest between the left carotid and subclavian arteries, and joins the left half of the deep part 428' of the epicardial plexus 420. Thus, supra-threshold stimulation of the left middle cervical ganglion 412' and/or the left superior cardiac nerve 436' will cause activation of nerves in the left half of the deep part 428' of the epicardial plexus 420. Of course, electrodes may be positioned to minimize and/or eliminate stimulation of certain nerves (e.g., parasympathetic, right sympathetic, etc.).

Left Inferior Cervical Ganglion and Left Inferior Cardiac Nerve

The left inferior cardiac nerve 440' arises from the left inferior cervical ganglion 416' or the left first thoracic ganglion (or left stellate ganglion, e.g., 416'). The left inferior cardiac nerve 440' descends behind the subclavian artery and along the front of the trachea, to join the deep part 428, 428' of the epicardial plexus 420. The left inferior cardiac nerve 440' communicates freely behind the subclavian artery with the recurrent nerve and the left middle cardiac nerve 436'. Thus, supra-threshold stimulation of the left inferior cervical ganglion 416' (or left stellate ganglion or left first thoracic ganglion) and/or the left inferior cardiac nerve 440' may also cause stimulation of the left middle cardiac nerve 412' and/or the recurrent nerve. Ultimately, supra-threshold stimulation of the left inferior cervical ganglion 416' (or left stellate ganglion or left first thoracic ganglion) and/or the left inferior cardiac nerve 440' will cause activation of nerves in the deep part 428, 428' of the epicardial plexus 420. Of course, electrodes may be positioned to minimize and/or eliminate stimulation of certain nerves (e.g., parasympathetic, right sympathetic, etc.).

Epicardial Left Sympathetic Pathways

As already mentioned, the left coronary subplexus (I), the ventral left atrial subplexus (IV), the left dorsal subplexus (V) and the middle dorsal subplexus (VI), should be considered as being supplied by nerves of the left side of the deep part 428' of the epicardial plexus and hence, in significant part, by at nerves from the left middle cervical ganglion 412' and the inferior left cervical ganglion 416' (e.g., left stellate ganglion or left first thoracic ganglion). Thus, according to various exemplary methods and/or devices described herein, direct stimulation of these epicardial subplexuses, and/or nerves extending from these subplexuses, will cause an increase in contractility.

Treatment for Long QT and/or Symptoms Thereof

Various exemplary methods and/or exemplary devices described herein are optionally suitable for treatment of long QT syndrome (LQTS), generally a repolarization disorder (e.g., a disease due to abnormalities in ion channels controlling action potentials myocardial cells). LQTS may involve an imbalance in the sympathetic nervous system or an intracardiac abnormality that causes an imbalance in the sympathetic nervous system (e.g., potassium regulation, etc.). In addition, LQTS may involve inadequate Q-T interval shortening for increasing heart rate. Treatment of various forms of LQTS may involve use of beta-blockers (adrenergic blockers), high thoracic left sympathectomy, left cardiac sympathetic denervation, right cardiac sympathetic denervation, etc. Yet others have used sodium channel blockers and found that an increase in sympathetic tone may protect LQTS patients from detrimental symptoms (e.g., palpitations, syncope, etc.). Thus, various exemplary methods and/or exemplary devices are optionally suitable for stimulation of sympathetic nerves and/or parasympathetic nerves to mitigate LQTS. For example, an exemplary method that stimulates sympathetic and/or parasympathetic nerves to maintain sympathetic tone may protect a LQTS patient from detrimental symptoms. Another exemplary method optionally stimulates parasympathetic nerves to offset surges in sympathetic tone and thereby protect a LQTS patient from detrimental symptoms. Of course, a variety of other methods are also possible wherein sympathetic and/or parasympathetic nerves are stimulated to aid LQTS patients (e.g., treat Q-T interval, symptoms, etc.).

Neural Stimulation

As described above, various parasympathetic and sympathetic nerves affect cardiac function. Thus, stimulation of such nerves can provide for cardiac control. Stimulation of autonomic nerves can require relatively high frequencies and high voltages. Such frequencies and/or voltages can quickly drain the battery of an implantable device and/or cause cardiac stimulation. As with all pulsing, the power is proportional to the voltage squared and directly proportional to the pulse frequency and the pulse width; hence power consumption increases rapidly with an increase in voltage. Therefore, control of voltage has a more direct effect on power consumption. According to various exemplary methods and/or devices, an algorithm for control of stimulation pulse power begins at a maximum power. In such methods and/or devices, if the maximum power does not affect cardiac function due to autonomic nerve stimulation then stimulation pulses at lower powers are unlikely to affect cardiac function. Hence, such an algorithm will terminate quickly in the case that the maximum power does not affect cardiac function and thus, conserve time and power. In addition, such an algorithm optionally adjusts pulse parameters to avoid cardiac capture.

Figure 5:
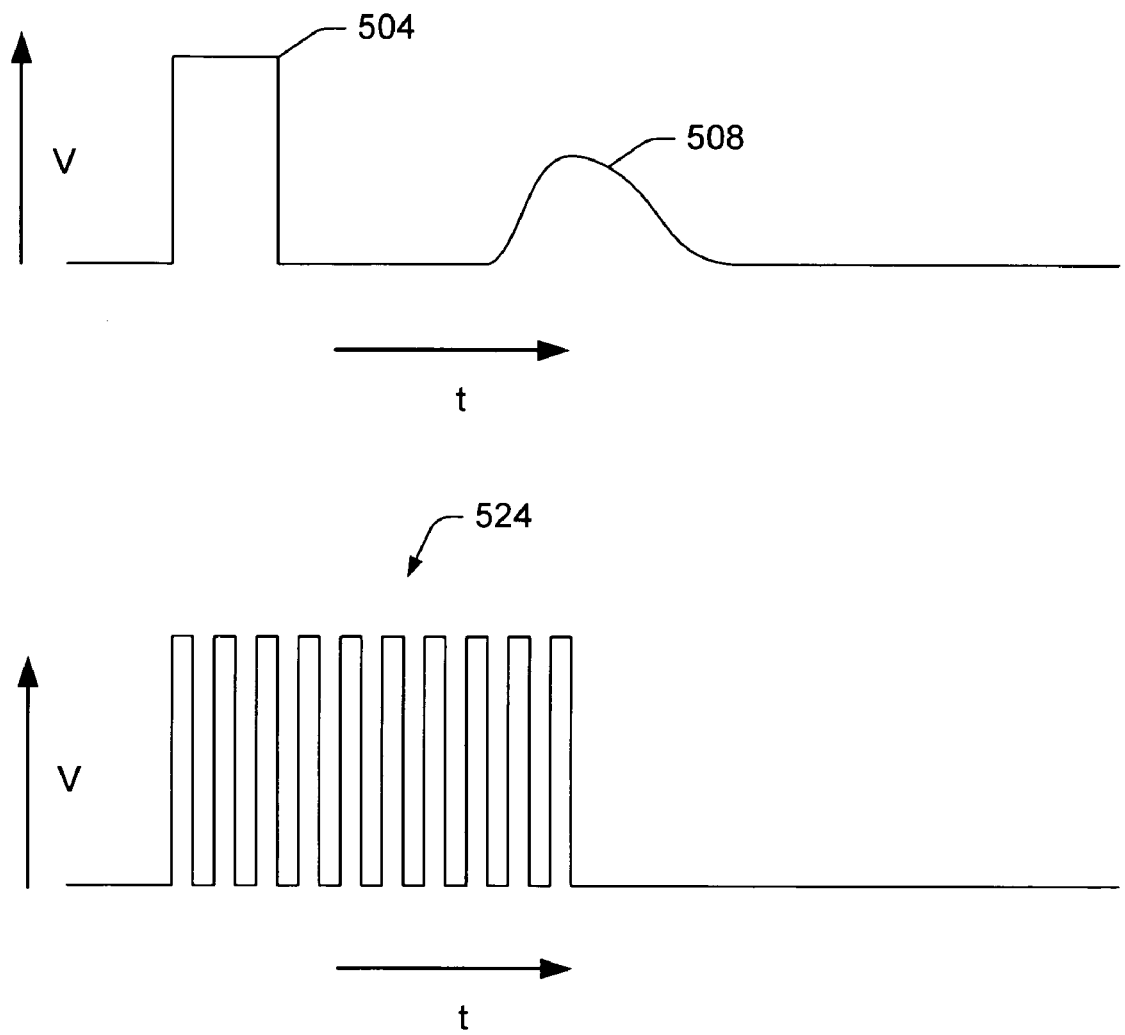
FIG. 5 is a diagram of a typical pacing pulse and a typical neural stimulation pulse shown as plots of voltage versus time.

Referring to FIG. 5, a typical pacing pulse 504 and a typical autonomic neural stimulation pulse train 524 are shown as plots of voltage versus time. In FIG. 5, the pacing pulse 504 is followed by an evoked response 508. Often, an auto-capture algorithm will rely on the evoked response 508 to properly set the amplitude and/or duration of the pacing pulse 504. In contrast, the exemplary autonomic pulse train 524, as shown in this example, does not cause an evoked response. In general, an autonomic pulse train should not cause an evoked response, such an evoked response it typically undesirable. In addition, delivery of a stimulus to an autonomic nerve (e.g., via an electrode, coil, etc.) usually aims to achieve an autonomic response. An autonomic response, in turn, may affect cardiac function.

Figure 6:
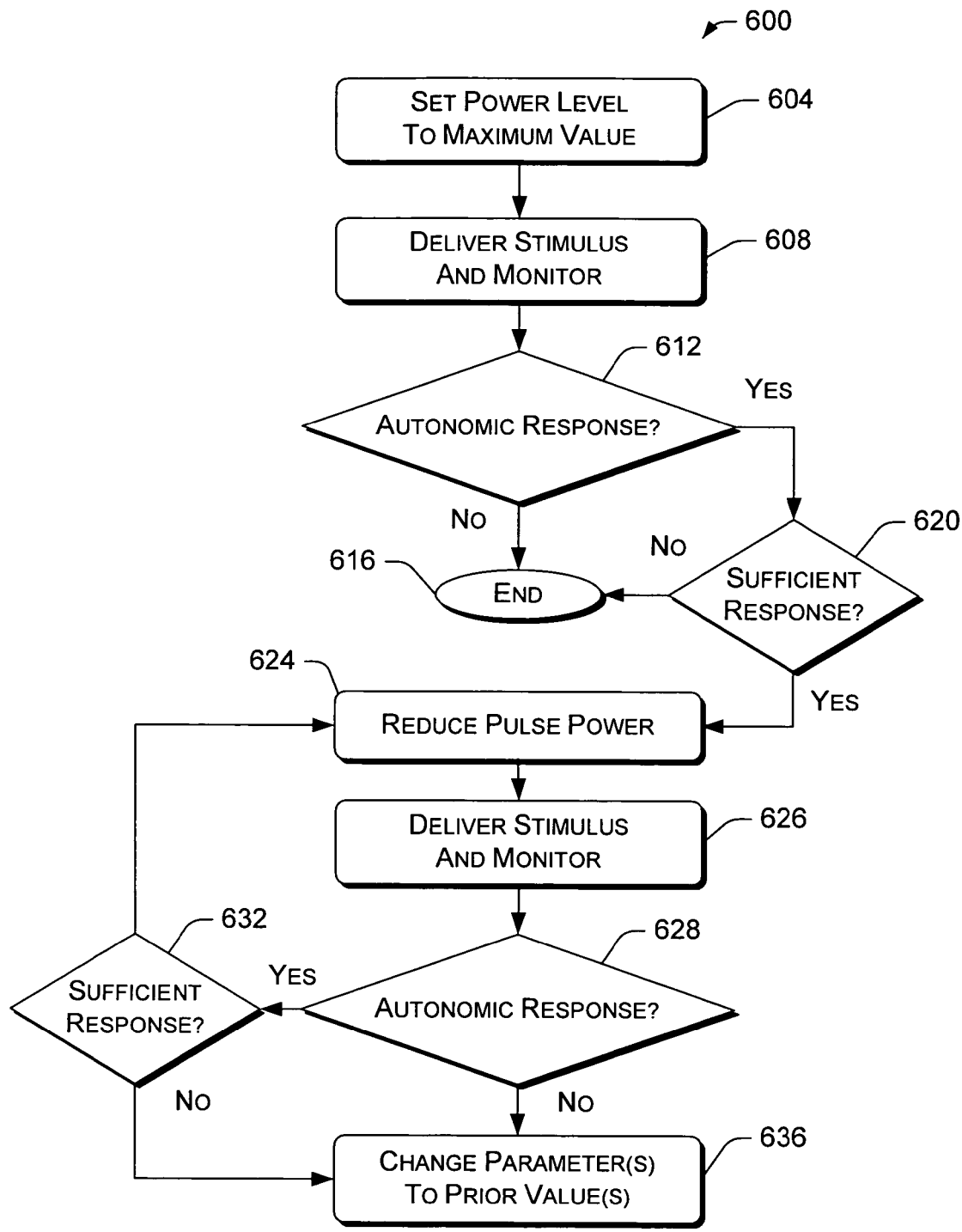
FIG. 6 is a block diagram of an exemplary method for stimulating autonomic nerves.

Referring to FIG. 6, an exemplary method for adjusting pulse parameters 600 is shown. In an initialization block 604, a user and/or a device set a pulse and/or a pulse train power level to a maximum value (or some other upper value). According to this exemplary method 600, an implantable device optionally stores maximum values (and/or other values) in memory in relation to a maximum level (and/or other level) of power consumption, which may be based at least in part on a desired power supply life. A delivery and monitoring block 608 follows the initialization block 604 wherein an implantable stimulation device delivers a pulse or pulses and monitors cardiac function. The delivery feature of the block 608 optionally delivers a plurality of pulse trains over a set period of time, which is optionally based on cardiac events. For example, the implantable device may (i) deliver a pulse train during a first refractory interval; (ii) wait a period of time; and (iii) deliver a second pulse train during second refractory interval. During and/or after such a delivery sequence, the implantable device also monitors cardiac function, in particular, cardiac function associated directly and/or indirectly with the autonomic nervous system. Details of cardiac functions are described above and include, but are not limited to, chronotropy, inotropy and dromotropy. Of course, other functions associated directly and/or indirectly with the autonomic nervous system may also be monitored.

After the delivery and monitoring block 608, the implantable device determines in a determination block 612 whether an autonomic response occurred due to the delivery of the stimulus or stimuli, which is usually detected as a change in cardiac function, in other words, whether the delivering achieved an autonomic response that affected cardiac function. If no autonomic response occurs (e.g., change in the cardiac function), then the method 600 terminates in an end block 616; however, if the determination block 612 determines that an autonomic response (e.g., change in the cardiac function) occurred, then in another determination block 620, the implantable device determines whether the response is sufficient. If the response is insufficient, then the method 600 terminates in the end block 616; however, if the response is sufficient, then the method 600 enters a power reduction scheme.

The power reduction scheme of the exemplary method 600 of FIG. 6 commences in a power reduction block 624. In the power reduction block 624, the implantable device reduces the pulse power by adjusting at least one of the pulse and/or pulse train parameters. As already mentioned, power varies with voltage squared and directly with pulse width and frequency. Thus, the implantable device may reduce power via an adjustment to voltage, pulse width, and/or frequency. Of course, a variety of other ways to reduce power also exist. More advanced algorithms optionally reduce one parameter (e.g., voltage) while increasing another (e.g., frequency) to effectuate an overall reduction in power.

Another delivery and monitoring block 626 follows the reduction block 624 wherein the implantable stimulation device delivers a pulse or pulses and monitors cardiac function. This particular block 626 optionally operates similarly to the delivery and monitoring block 608. In yet another determination block 628, the implantable device determines whether an autonomic response (e.g., a change in the cardiac function) occurred due to the stimulus or stimuli, or in other words, whether the stimulus achieved an autonomic response. If no response occurred, then in a parameter adjustment block 636, the implantable device changes the parameters back to their values as set prior to the power reduction block 624 (or last pass to the power reduction block 624). According to this exemplary method 600, the implantable device then uses these parameters for delivering a stimulus or stimuli. In the case that the stimulus achieved an autonomic response (e.g., a change in the cardiac function), the implantable device, in another determination block 632, the device determines whether the response is sufficient. Sufficiency is generally measured with respect to some cardiac function and/or with respect to some therapeutic measure. If the response is sufficient, then the method 600 continues to the power reduction block 624. However, if the response is insufficient, then, in the parameter adjustment block 636, the implantable device sets the parameters back to their values as set prior to the power reduction block 624 (or last pass to the power reduction block 624). Ultimately, the exemplary method 600 adjusts stimulus and/or stimuli parameters to conserve power.

In an implementation of the exemplary method 600, the voltage is set at a maximum voltage and the frequency is set at a maximum frequency while pulse width is set at the expected chronaxie for the autonomic nerve in question. Next, an implantable stimulation device delivers stimuli to an autonomic nerve for two seconds. During this time, the device also acquires data indicative of cardiac function. For example, if the autonomic nerve is the right vagus nerve, then the data is preferably indicative of SA node rate, in particular, capable of indicating a reduction in SA node rate. As another example consider stimuli delivered to the left coronary epicardiac plexus. In such an example, the data is preferably indicative of inotropy, in particular, capable of indicating an increase in inotropy. Again, through such exemplary procedures, a determination is optionally made as to whether a stimulus achieved an autonomic response that affected cardiac function.

If the acquired data indicate the there is no autonomic response (e.g., change in the cardiac function) then the method terminates. However, if there is an autonomic response, then a determination is made to determine whether the response is sufficient, e.g., whether the response is of therapeutic interest. In the case that the response is sufficient, then power may be excessive; thus, in turn, for example, an approximately 5 percent reduction in voltage and an approximately 10 percent reduction in frequency are made. In this particular example, voltage is reduced by a smaller percentage due to the fact that power is proportional to the voltage squared.

After the reductions, the implantable device delivers stimuli and monitors cardiac function. If there is a continuing and sufficient autonomic response, then further reductions in power are made. However, if there is no response and/or the response is insufficient, then the pulse parameters are reset.

Various exemplary methods described herein, and/or equivalents thereof, optionally implement an exemplary method for avoiding cardiac capture. Referring to FIG. 7, an exemplary method for avoiding cardiac capture 700 is shown. In a delivery and monitoring block 704, an implantable stimulation device delivers a stimulus or stimuli to autonomic nerves and monitors cardiac and/or other circulatory system functions. In a determination block 708, the implantable device determines whether the stimulus and/or stimuli have caused cardiac capture. For example, the device may monitor ventricular activity for the presence of an evoked response. The device may compare the timing of the evoked response to determine whether the evoked response was caused by an autonomic stimulus or by a pacing stimulus. Again, an evoked response caused by an autonomic stimulus is generally an undesirable evoked response.

In the case that the evoked response was caused by an autonomic stimulus, then in a reduction block 712, the implantable device reduces the pulse width and increases the pulse frequency of the autonomic stimulation pulse. For example, the device may reduce the pulse width by approximately 20 percent and increase the frequency by approximately 20 percent. While such an adjustment to pulse parameters maintains a constant charge to the autonomic nerve as well as a constant power usage, the risk of cardiac capture decreases because the time constant for autonomic nerves is typically less than that of the myocardium. After a reduction in pulse width and an increase in pulse frequency, the method 700 returns to the delivery and monitoring block 704.

Coordinated Auto-Capture of Multiple Autonomic Nerves

Figure 8:
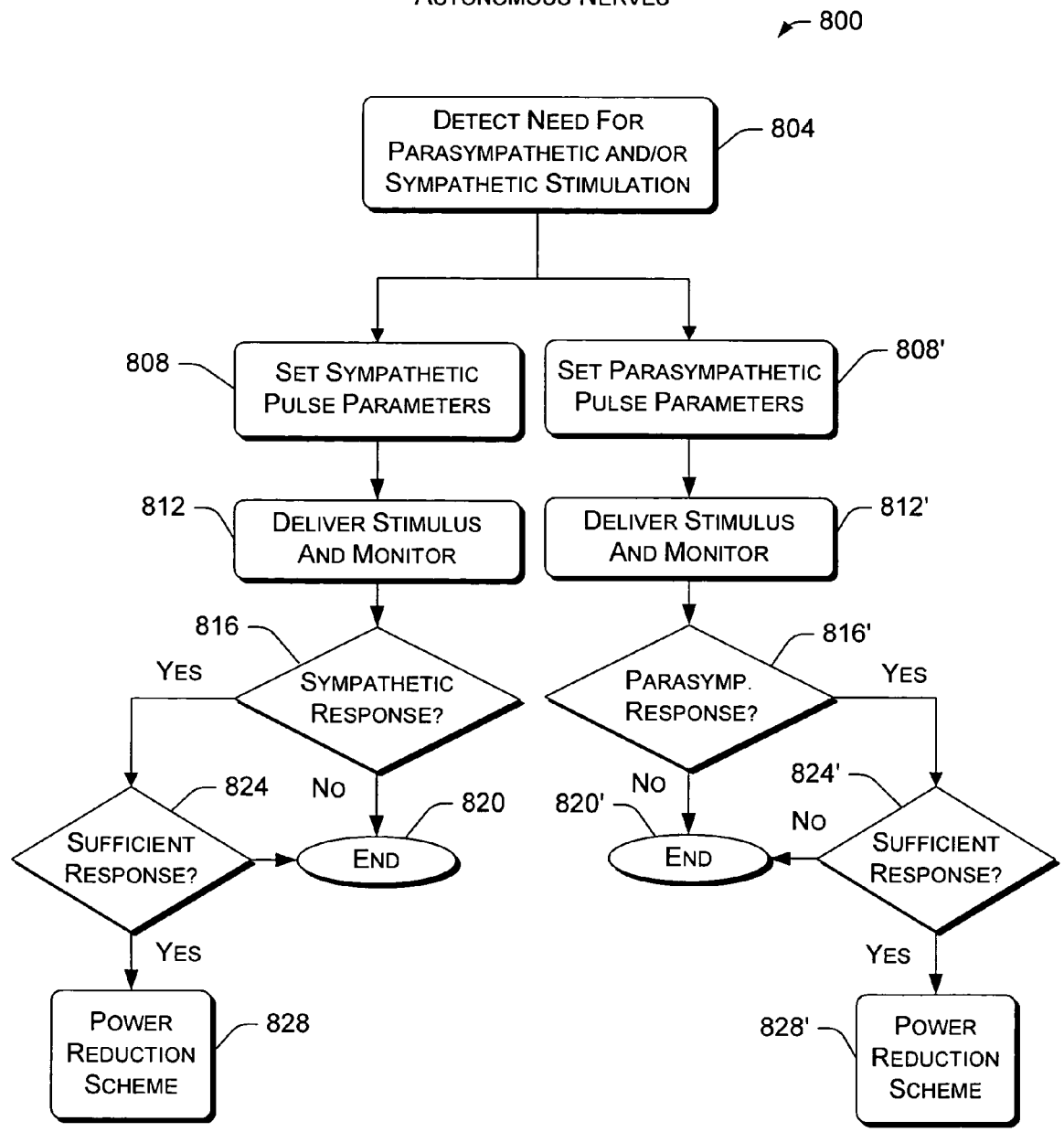
FIG. 8 is a block diagram of an exemplary method for parasympathetic and/or sympathetic nerves.

In some circumstances, a device may stimulate sympathetic nerves and parasympathetic nerves to affect chronotropy, inotropy and/or dromotropy. FIG. 8 shows a block diagram of an exemplary method 800 for coordinated stimulation of a parasympathetic nerve and a sympathetic nerve. In a detection block 804, an implantable stimulation device detects a need for parasympathetic and/or sympathetic nerve stimulation. In parameter set blocks 808, 808', the implantable device sets stimulation parameters for sympathetic and/or parasympathetic nerves. Next, in delivery and monitoring blocks 812, 812', the implantable device delivers a stimulus to parasympathetic and/or sympathetic nerves and monitors cardiac functions. Determination blocks 816, 816' follow wherein the implantable device determines whether a sympathetic or a parasympathetic response has occurred. If no response occurs, then the exemplary method 800 terminates in either a sympathetic end block 820 or a parasympathetic end block 820'. Alternatively, one leg may terminate and the other may continue. If a response does occur, then a determination block 824 or 824' follows together with a respective power reduction scheme 828 or 828'. A suitable exemplary power reduction scheme was discussed above with respect to the method 600 of FIG. 6.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein sympathetic tuning via sympathetic nerve stimulation aims to increase heart rate. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory increase in heart rate (e.g., an increase of therapeutic value). In this exemplary method, for example, a physician may slowly move a lead throughout an appropriate region and deliver pulses until a desired increase in heart rate is seen maximally via monitoring.

In yet another exemplary method, a lead and/or an electrode are optionally positioned to increase contractility due to sympathetic nerve stimulation while at the same time minimizing stimulation effects on heart rate. Once a "sweet spot" is found, then pulse parameters are optionally adjusted to minimize electrical power consumption, for example, by previously mentioned exemplary methods. The aforementioned exemplary methods also apply to parasympathetic stimulation except that the aim of stimulation would generally differ.

Figure 9:
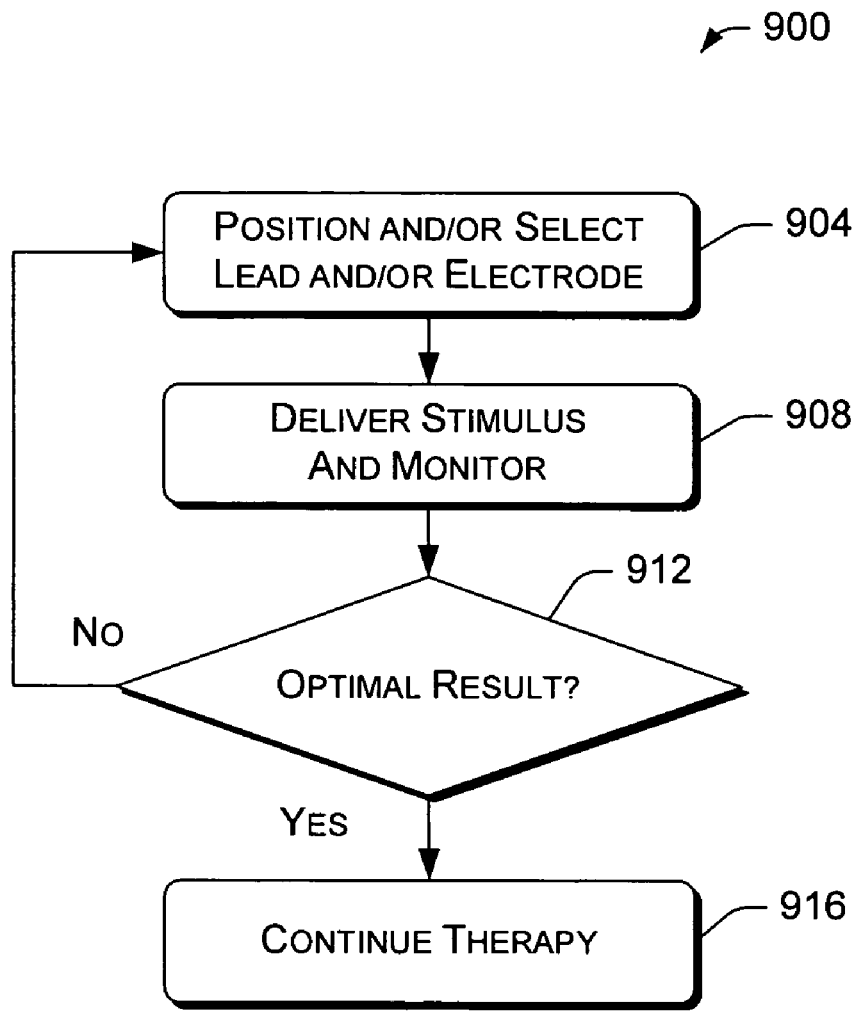
FIG. 9 is a block diagram of an exemplary method for positioning and/or selecting a lead and/or an electrode.

Referring to FIG. 9, a block diagram of an exemplary method for positioning and/or selecting a lead and/or an electrode 900 is shown. In a positioning and/or selecting block 904, a device and/or a user positions and/or selects a lead and/or an electrode to deliver a pulse (or pulses) in an effort to stimulate an autonomic nerve (or nerves). For example, autonomic nerve stimulation may occur through use of a plurality of leads and/or a plurality of electrodes. In addition, a user may select one or more of the plurality of leads based on performance and/or select one or more of the plurality electrodes based on performance. Once positioning and/or selecting has been made, a delivery and monitoring block 908 follows wherein a stimulus or stimuli are delivered via the selected and/or positioned lead and/or electrode. After the delivery and monitoring block 908, a determination block 912 follows wherein a user and/or a device determines whether an optimal result was obtained in response to the delivering. If the result is not optimal, then the exemplary method 900 continues by returning to the positioning and/or selecting block 904. Of course, after some number of iterations, a user and/or device may determine which, if any, of the positioning and/or selecting iterations produced an optimal and/or satisfactory result. Once an optimal result is identified or produced, then appropriate therapy continues in a continuation block 916, wherein, for example, the implantation procedure and/or the therapy continues.

Thus, according to various exemplary methods and/or devices described herein, neural auto-capture and/or adjustment of neural stimulation parameters are possible. Such methods and/or devices are suitable for stimulation of parasympathetic and/or sympathetic nerves.

CONCLUSION

Although various exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method for delivering power to an electrode for stimulating an autonomic nerve to affect heart activity, comprising:
   delivering power to the electrode at a power level;
   determining whether the delivering achieved an autonomic response that affected cardiac contractility; and
   delivering power to the electrode at a reduced power level if the delivering achieved an autonomic response that affected the cardiac contractility.

2. The method of claim 1, wherein the power level comprises a maximum power level based at least in part on power limitations of an implantable device.

3. The method of claim 1, wherein the power level comprises a maximum power level based at least in part on battery life of an implantable device.

4. The method of claim 1, wherein the autonomic nerve is a parasympathetic nerve.

5. The method of claim 4, wherein the determining determines whether the delivering decreased heart rate.

6. The method of claim 4, wherein the determining determines whether the delivering decreased dromotropy.

7. The method of claim 4, wherein the determining determines whether the delivering decreased inotropy.

8. The method of claim 1, wherein the autonomic nerve is a sympathetic nerve.

9. The method of claim 8, wherein the determining determines whether the delivering increased heart rate.

10. The method of claim 8, wherein the determining determines whether the delivering increased inotropy.

11. The method of claim 8, wherein the determining determines whether the delivering increased dromotropy.

12. The method of claim 1, wherein the reduced power level is determined by reducing a parameter and wherein the parameter comprises at least one parameter selected from the group consisting of amplitude, frequency, voltage, current, energy, charge, power, number of pulses and pulse width.

13. The method of claim 1, wherein the determining determines whether the delivering caused an undesirable evoked response.

14. One or more computer-readable media having computer-readable instructions thereon which, when executed by a programmable stimulation device, causes a stimulation device to deliver power to an electrode for stimulating an autonomic nerve to affect heart activity, said instructions including code for:
   delivering power to the electrode at a power level;
   determining whether the delivering achieved an autonomic response that affected cardiac contractility; and
   delivering power to the electrode at a reduced power level if the delivering achieved an autonomic response that affected the cardiac contractility.

15. A method for delivering power to an electrode for stimulating an autonomic nerve to affect cardiac function, comprising:
   delivering power to the electrode at a pulse width and at a frequency;
   determining whether the delivering caused an undesirable evoked response; and
   delivering power to the electrode at a reduced pulse width and at an increased frequency if the delivering caused an undesirable evoked response.

16. The method of claim 15, wherein the delivering at a pulse width and at a frequency and the delivering at a reduced pulse width and at an increased frequency both deliver approximately the same power.

17. The method of claim 15, wherein the determining further comprises determining whether the delivering affected chronotropy, inotropy, and/or dromotropy.

18. The method of claim 15, wherein the delivering further comprising reducing the power to the electrode if the delivering affected chronotropy, inotropy, and/or dromotropy.

19. One or more computer-readable media having computer-readable instructions thereon which, when executed by a programmable stimulation device, causes a stimulation device to deliver power to an electrode for stimulating an autonomic nerve to affect cardiac function, said instructions including code for:
   delivering power to the electrode at a pulse width and a frequency;
   determining whether the delivering caused an undesirable evoked response; and
   delivering power to the electrode at a reduced pulse width and at an increased frequency if the delivering caused an undesirable evoked response.

20. An implantable stimulation device for stimulating an autonomic nerve to affect cardiac function, comprising:
   an electrode configured to deliver a stimulation pulse to an autonomic nerve at a power level;

a sensor configured to acquire data on cardiac contractility in response to the stimulation pulse;

a controller configured to reduce the power level to a reduced power level if the cardiac contractility changed in response to the stimulation pulse.

21. The device of claim 20, wherein the power level is a maximum power level.

22. The device of claim 21, wherein the maximum power is based at least in part on power supply life.

23. The device of claim 20, wherein the stimulation pulse comprises an amplitude, a frequency, and a pulse width.

24. The device of claim 23, wherein the controller is further configured to increase the frequency of the stimulation pulse and to decrease the pulse width of the stimulation pulse if the stimulation pulse caused an undesirable evoked response.

25. The device of claim 20 wherein the device comprises a pressure sensor adapted to sense pressure in a right ventricle and to generate an electrical pressure signal corresponding to the sensed pressure.

26. A method for positioning an electrode comprising:
delivering power to the electrode at a power level;
determining whether the delivering affected cardiac function due to stimulation of an autonomic nerve; and
repositioning the electrode if the delivering did not affect the cardiac function or delivering power to the electrode at a reduced power level if the delivering affected the cardiac function.

27. A method for selecting an electrode comprising:
delivering power to the electrode at a power level;
determining whether the delivering affected cardiac function due to stimulation of an autonomic nerve; and
selecting another electrode if the delivering did not affect the cardiac function or delivering power to the electrode at a reduced power level if the delivering affected the cardiac function.

28. An implantable stimulation device for stimulating an autonomic nerve to affect cardiac function, comprising:
electrode means for delivering a stimulation pulse to an autonomic nerve at a maximum power level based at least in part on power limitations or battery life of the implantable stimulation device;
sensor means for acquiring data on cardiac function in response to the stimulation pulse;
controller means for reducing the power level to a reduced power level if the cardiac function changed in response to the stimulation pulse.

29. The implantable stimulation device of claim 28, wherein the autonomic nerve is a parasympathetic nerve.

30. The implantable stimulation device of claim 29, wherein the determining determines whether the delivering decreased heart rate.

31. The implantable stimulation device of claim 29, wherein the determining determines whether the delivering decreased dromotropy.

32. The implantable stimulation device of claim 29, wherein the determining determines whether the delivering decreased inotropy.

33. The implantable stimulation device of claim 28, wherein the autonomic nerve is a sympathetic nerve.

34. The implantable stimulation device of claim 33, wherein the determining determines whether the delivering increased heart rate.

35. The implantable stimulation device of claim 33, wherein the determining determines whether the delivering increased inotropy.

36. The implantable stimulation device of claim 33, wherein the determining determines whether the delivering increased dromotropy.

* * * * *